(12) United States Patent
Utsunomiya et al.

(10) Patent No.: US 9,033,500 B2
(45) Date of Patent: May 19, 2015

(54) OPTICAL COHERENCE TOMOGRAPHY AND METHOD THEREOF

(75) Inventors: Norihiko Utsunomiya, Machida (JP); Junko Nakajima, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/805,805

(22) PCT Filed: Jun. 22, 2011

(86) PCT No.: PCT/JP2011/064853
§ 371 (c)(1),
(2), (4) Date: Dec. 20, 2012

(87) PCT Pub. No.: WO2012/002406
PCT Pub. Date: Jan. 5, 2012

(65) Prior Publication Data
US 2013/0093997 A1    Apr. 18, 2013

(30) Foreign Application Priority Data

Jun. 30, 2010  (JP) ................................. 2010-150261

(51) Int. Cl.
*A61B 3/10*    (2006.01)
*A61B 3/14*    (2006.01)
*A61B 3/12*    (2006.01)

(52) U.S. Cl.
CPC . *A61B 3/12* (2013.01); *A61B 3/102* (2013.01); *A61B 3/14* (2013.01)

(58) Field of Classification Search
USPC .......... 351/205, 206, 221, 246; 356/450–479; 382/131; 600/407, 425
See application file for complete search history.

(56) References Cited

U.S. PATENT DOCUMENTS

| 7,510,282 B2 | 3/2009 | Ueno et al. |
| 7,639,845 B2 | 12/2009 | Utsunomiya |
| 7,648,242 B2 | 1/2010 | Ferguson et al. |
| 7,866,821 B2 | 1/2011 | Ferguson et al. |

(Continued)

FOREIGN PATENT DOCUMENTS

| JP | 11-253403 A | 9/1999 |
| JP | 2007-130403 A | 5/2007 |

(Continued)

OTHER PUBLICATIONS

Michael Pircher, et al., "Simultaneous SLO/OCT imaging of the human retina with axial eye motion correction", Optics Express, OSA (Optical Society of America), Washington, D.C. (US), vol. 15, No. 25, Dec. 10, 2007, XP-002639069, pp. 16922-16932.

(Continued)

*Primary Examiner* — Mahidere Sahle
(74) *Attorney, Agent, or Firm* — Fitzpatrick, Cella, Harper & Scinto

(57) ABSTRACT

The image sensing apparatus comprises a first scan unit for scanning light from an OCT light source and light from an SLO light source in a first direction of a test object, and a second scan unit for scanning the light from the OCT light source in a second direction different from the first direction of the test object. The image sensing apparatus acquires tomographic images of the test object along the first direction when the first scan unit scans the light from the OCT light source, and acquires cross-over images of the test object corresponding to the tomographic images when the first scan unit scans the light from the SLO light source.

23 Claims, 8 Drawing Sheets

(56) References Cited

U.S. PATENT DOCUMENTS

| | | | |
|---|---|---|---|
| 8,033,665 B2 | 10/2011 | Ferguson et al. |
| 8,294,901 B2 | 10/2012 | Yoshida et al. |
| 8,330,808 B2 | 12/2012 | Satake |
| 8,358,421 B2 | 1/2013 | Utsunomiya |
| 8,801,180 B2 | 8/2014 | Hayashi et al. |
| 2006/0158655 A1 | 7/2006 | Everett et al. |
| 2007/0263171 A1 | 11/2007 | Ferguson et al. |
| 2008/0024721 A1 | 1/2008 | Ueno et al. |
| 2010/0073634 A1 | 3/2010 | Ferguson et al. |
| 2010/0110171 A1 | 5/2010 | Satake |
| 2010/0142780 A1 | 6/2010 | Yasuno et al. |
| 2011/0032479 A1 | 2/2011 | Utsunomiya |
| 2011/0080561 A1 | 4/2011 | Hayashi et al. |
| 2011/0085136 A1 | 4/2011 | Ferguson et al. |
| 2011/0176107 A1 | 7/2011 | Yoshida et al. |
| 2011/0267580 A1 | 11/2011 | Nakajima et al. |
| 2011/0267581 A1 | 11/2011 | Nakajima et al. |
| 2012/0002166 A1 | 1/2012 | Tomatsu et al. |
| 2012/0062843 A1 | 3/2012 | Ferguson et al. |
| 2013/0021575 A1 | 1/2013 | Yoshida et al. |

FOREIGN PATENT DOCUMENTS

| | | |
|---|---|---|
| JP | 3964035 B2 | 8/2007 |
| JP | 2008-029467 A | 2/2008 |
| JP | 2009-535164 A | 10/2009 |
| JP | 2010-000191 A | 1/2010 |
| JP | 2010-110392 A | 5/2010 |
| WO | 2005/077255 A1 | 8/2005 |
| WO | 2007/130411 A2 | 11/2007 |
| WO | 2009/059034 A1 | 5/2009 |
| WO | 2009/095473 A1 | 8/2009 |

OTHER PUBLICATIONS

Nov. 25, 2011 International Search Report and Written Opinion in International Patent Appln. No. PCT/JP2011/064853.

Jul. 29, 2014 Chinese Official Action in Chinese Patent Appln. No. 201180032938.6.

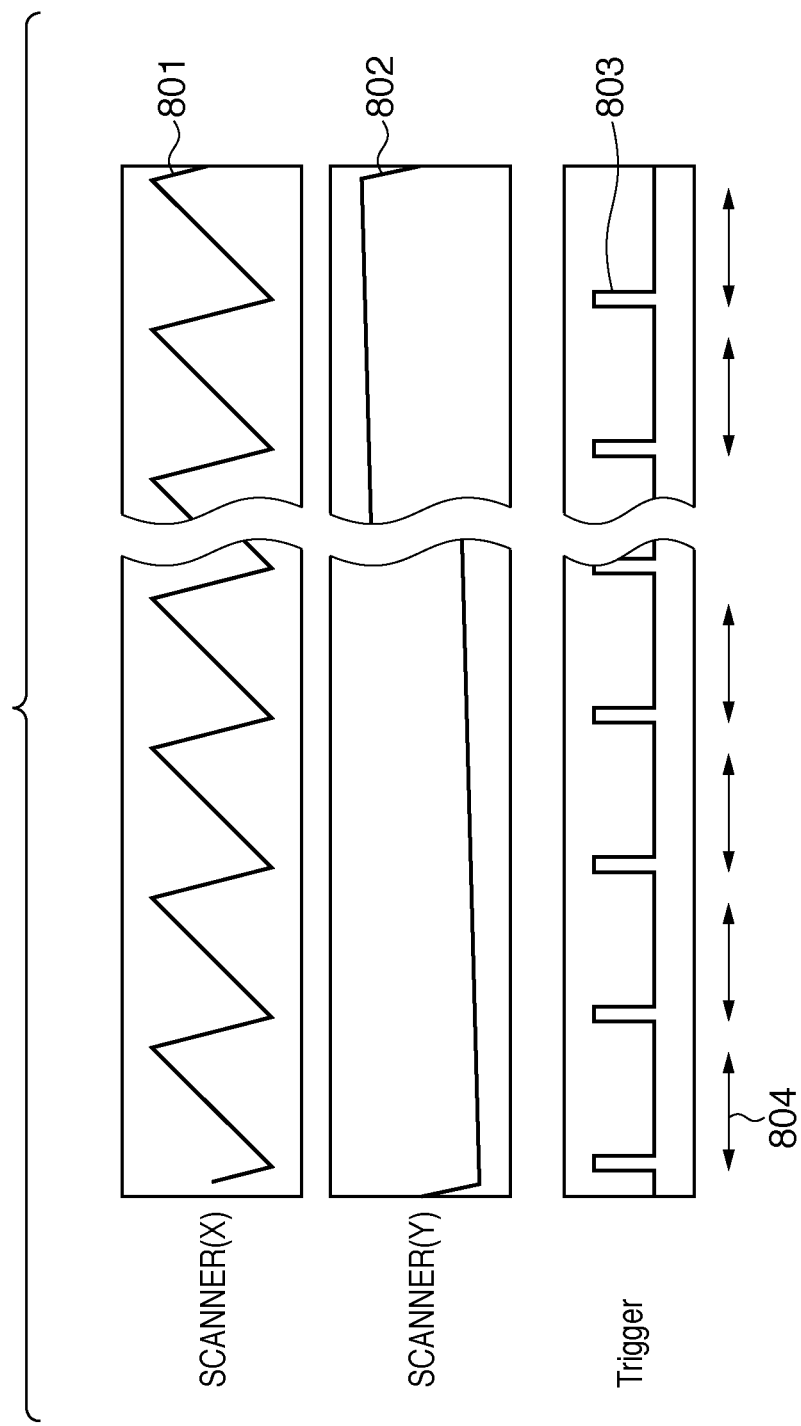

OPTICAL COHERENCE TOMOGRAPHY AND METHOD THEREOF

TECHNICAL FIELD

The present invention relates to an optical coherence tomography and control method thereof, and more specifically, relates to the optical coherence tomography which has a low coherent light interference optical system that is specifically used for ophthalmological medical examination and others, and the control method thereof.

BACKGROUND ART

Various optical equipment have been used as ophthalmological equipment. Among the equipment, the following optical equipment have been utilized to examine an eye:
Anterior imaging equipment
Fundus camera
Scanning Laser Ophthalmoscope (SLO)
Optical coherence tomography (OCT) utilizing light interference due to low coherent light and other equipment have been used.

Particularly, the optical coherence tomography utilizing light interference because of low coherent light is equipment that is used to acquire a high-resolution fundus tomographic image and has been essential equipment in a specialized retina out-patient clinic. Hereafter, such an optical coherence tomography is described as OCT equipment in short.

The OCT equipment is the equipment with an interferometer to measure with high sensitivity reflected light from a sample by irradiating the sample represented by the retina with low coherent light. Further, the OCT equipment can obtain a tomographic image by scanning the low coherent light over the sample. Specifically, a retina tomographic image is utilized extensively for ophthalmologic diagnosis.

An image with three-dimensional structure can be acquired by continuously acquiring multiple tomographic images when tomographic images are shot by the OCT equipment. However, the time for acquiring the image with a three-dimensional structure becomes long compared to that for acquiring one tomographic image because of shooting the images by scanning multiple tomographic images. Therefore, the image with a three-dimensional structure that is to be acquired must be distorted or displaced when an eyeball moves during the shooting. An eyeball of a subject being tested keeps moving with involuntary movement of the eyeball, so called "involuntary eye movement" even if he/she attempts to see one point. To solve these problems, an OCT proposed in Patent Laid-Open No. 2007-130403 (hereafter, Document 1) corrects a shifted image by aligning an image produced by integrating three dimensional tomographic images in depth direction of a fundus with a two dimensional image of the fundus surface which is acquired by an external means.

As described above, Document 1 shows that if the examined eye moves while shooting an retina image with three dimensional structure, the shifted image is corrected by aligning it with the fundus surface image. However, it is to be hoped that the OCT equipment could prevent the shifted image with high accuracy as it has been highly desirable to have high resolution and high repeatability. With regard to eye movement, there is not only a linear eyeball movement in two directions through the line-of-sight but also circumnutating of rotating about a visual axis. That is, an eyeball has three degrees of freedom. Document 1 does not describe the eyeball movement in three-degrees of freedom as described above every time each of the tomographic images is acquired (scanned).

SUMMARY OF INVENTION

In order to solve the above problems, one of the embodiments of the present invention provides an optical coherence tomography, which enables the variation of tomographic images generated by the movement of the examined eye to be corrected with higher accuracy during shooting by utilizing multiple tomographic images acquired by the optical coherence tomography using light interference.

According to one aspect of the present invention, there is provided an image sensing apparatus comprising: first scan means for scanning light from an OCT light source and light from an SLO light source in a first direction of a test object; second scan means for scanning the light from the OCT light source in a second direction different from the first direction of the test object; first acquisition means for acquiring tomographic images of the test object along the first direction when the first scan means scans the light from the OCT light source; and second acquisition means for acquiring cross-over images of the test object corresponding to the tomographic images when the first scan means scans the light from the SLO light source.

Further, features of the present invention will become apparent from the following description of exemplary embodiments with reference to the attached drawings.

BRIEF DESCRIPTION OF DRAWINGS

FIG. 8 shows a scan-signal wave of a scanner of the optical coherence tomography in the second embodiment.

DESCRIPTION OF EMBODIMENTS

First Embodiment

An image sensing apparatus in this embodiment comprises a first acquisition unit for acquiring multiple tomographic images by repeatedly moving its shooting position (topographic profile-position) of the topographic image along a first direction to a second direction, a second acquisition unit for acquiring a two dimensional fundus image and a control unit for controlling these units. In this embodiment, an OCT imaging unit is used as the first acquisition unit and SLO imaging unit is used as the second acquisition unit. Each element of the optical coherence tomography is described below. In addition, although the ophthalmic equipment used for ophthalmological medical examination is described, the present invention can also be applied to endoscopic instruments to observe cutis and others.

(Optical Structure of OCT Imaging Unit)

Figure 1:
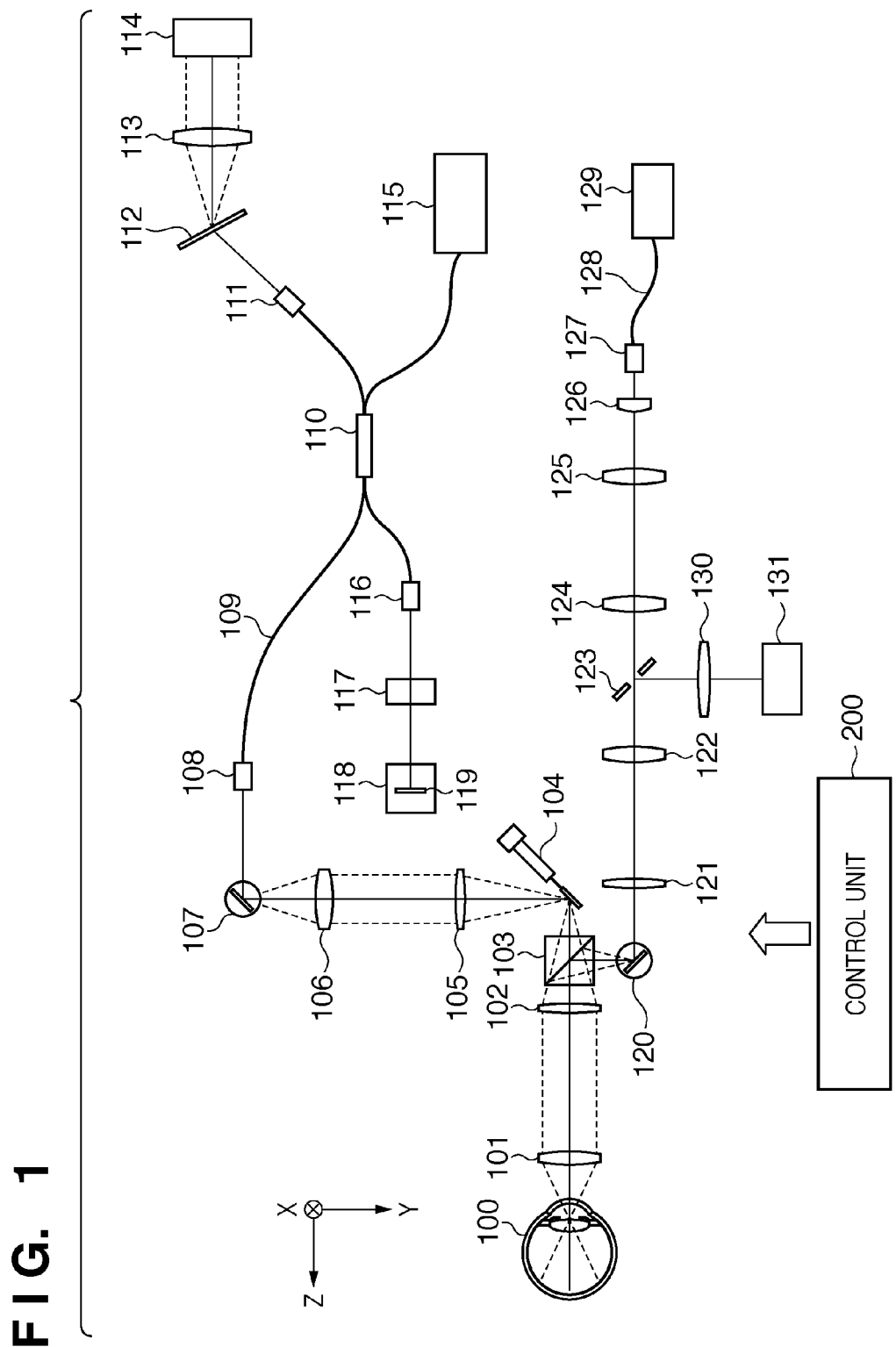
FIG. 1 shows an exemplary configuration for an optical system of optical coherence tomography in first embodiment.

The optical structure of OCT imaging unit, the first acquisition unit in the first embodiment is described referring to FIG. 1. FIG. 1 shows the structure of optical system of optical coherence tomography in first embodiment. An SLD (Super Luminescent Diode) light source, an ASE (Amplified Spontaneous Emission) light source or other light source is used as a low coherent light source 115 which is one example of an OCT light source. Moreover, SS (Swept Source) light source can also be used, and if it is used, a system structure must be in SS-OCT configuration which is different from the structure in FIG. 1, as known by one skilled art. One of the wavelengths of 850 nm and 1050 nm which is optimally suited to imaging a fundus uses a low coherent light generated by the low coherent light source 115. In this embodiment, it is assumed that a SLD light source with a central wavelength of 840 nm and a wavelength-half width of 45 nm is utilized for the low coherent light source 115.

Low coherent light emitted from the low coherent light source 115 passes through a fiber coupler 110 and is split into measurement light and reference light. Although the structure of interferometer using an optical fiber is described in this example, the structure of spatial light-optical system using a beam splitter may be used.

The measurement light in the form of parallel light is emitted from a fiber collimator 108 through a optical fiber 109. Moreover, the measurement light is incident upon an examined eye 100, one example of examined materials after it passes through an OCT scanner (Y) 107, relay lenses 106, 105 and an OCT scanner (X) 104, is transmitted into a dichroic beam splitter 103 and further passes through a scan lens 102 and an eyepiece lens 101. Wherein, a galvano-scanner is used for the OCT scanner (X) 104 and OCT scanner (Y) 107. The measurement light incident over the examined eye 100 reflects on a retina and returns to the fiber coupler 110 through the same optical path. In addition, X-direction and Y-direction for this embodiment are defined as shown in FIG. 1. Tomographic information in Z-direction (A-scan image) along the direction of optical axis is acquired based on interference light generated by the measurement light and reference light. Further, the B-scan image (a two-dimensional tomographic image in X-Z plane) on which the tomographic information (A-scan image) is arranged in X-direction by scanning the measurement light in X-direction using the OCT scanner (X) 104. Moreover, multiple B-scan images arranged in Y-direction are acquired by scanning the measurement light in Y-direction using the OCT scanner (Y) 107, and a three-dimensional tomographic image is finally acquired by combining these images.

The reference light is guided from the fiber coupler 110 to the fiber collimator 116, and it is emitted after becoming a parallel light. The reference light emitted from the fiber collimator 116 reflects on a reference mirror 119 arranged in a light path-length variable stage 118 after passing through a dispersion correction glass 117. The reference light reflected from the reference mirror 119 returns to the fiber coupler 110 after passing through the same light path.

The measurement light and reference light returned to the fiber coupler 110 are guided to the fiber collimator 111 after they are combined by the fiber coupler 110. Here, the combined light is defined as interference light. A spectrometer comprises the fiber collimator 111, a grating 112, a lens 113 and a line sensor 114. The spectrometer measures the interference light as intensity information corresponding to every wavelength. That is, the OCT imaging unit in this embodiment uses a spectrum domain scheme.

(Optical Structure of SLO Imaging Unit)

Next, the optical structure of SLO imaging unit, the second acquisition unit is described in a similar way referring to FIG. 1.

A semiconductor laser or SLD light source can preferably be used as a laser light source 129 which is one example of SLO light source. In addition, the wavelength of the laser light source 129 may be any wavelength in which the dichroic beam splitter 103 (means for splitting wavelength) can split the wavelength of light emitted by the low coherent light source 115. Generally, a wavelength region from 700 nm to 1000 nm is preferably used for better quality of fundus observational images. In this embodiment, the semiconductor laser emitting light with a wavelength of 760 nm is used as the laser light source 129.

Laser light emitted from the laser light source 129 becomes a parallel light after passing through a fiber collimator 127 via an optical fiber 128 and it is incident upon a cylinder lens 126. The cylinder lens 126 transforms the incident parallel light to a beam which linearly spreads toward the X-direction. Although the cylinder lens is used in this embodiment, any optical element which generates a line beam, for example, a line beam shaper using a Powell lens or a diffraction optical element can be utilized.

A line beam (SLO beam) which is spread in X-direction by the cylinder lens 126 passes through a center of a ring mirror 123 via relay lenses 125, 124, and is guided to an SLO scanner (Y) 120 after passing through relay lenses 121,122. A galvano scanner is used as the SLO scanner (Y) 120. Further, the line beam is reflected on a dichroic beam splitter 103 and is incident on the examined eye 100 after passing through the scan lens 102 and the eyepiece lens 101. The dichroic beam splitter 103 is configured to transmit the OCT beam and to reflect the SLO beam. In this embodiment, it has a film which transmits the light with wavelengths equal to or greater than 800 nm and reflects light with wavelengths below 770 nm.

The fundus of the examined eye 100 is irradiated with the SLO beam incident on the examined eye 100, which is a beam radially extended in the X-direction (line beam). The line beam is reflected or scattered on the fundus of the examined eye and is returned to the ring mirror 123 after passing through the same light path. Because the position of the ring mirror 123 is conjugate with the pupil position of the examined eye, light passing through the peripheral part of the pupil among the back scattering light of the line beam irradiated on the fundus is reflected on the ring mirror 123 and forms an image on the line sensor 131 after passing through a lens 130. Although the SLO imaging unit is described in this embodiment so that it is configured with the line scan-SLO using a line beam, it may also be configured with a flying spot-SLO. In this case, light emitted from the laser light source 129 should be scanned in X, Y-direction. Imaging operations using the optical system of OCT imaging unit and the optical system of SLO imaging unit are controlled by the control unit 200.

(Structure of Control Unit)

Figure 2:
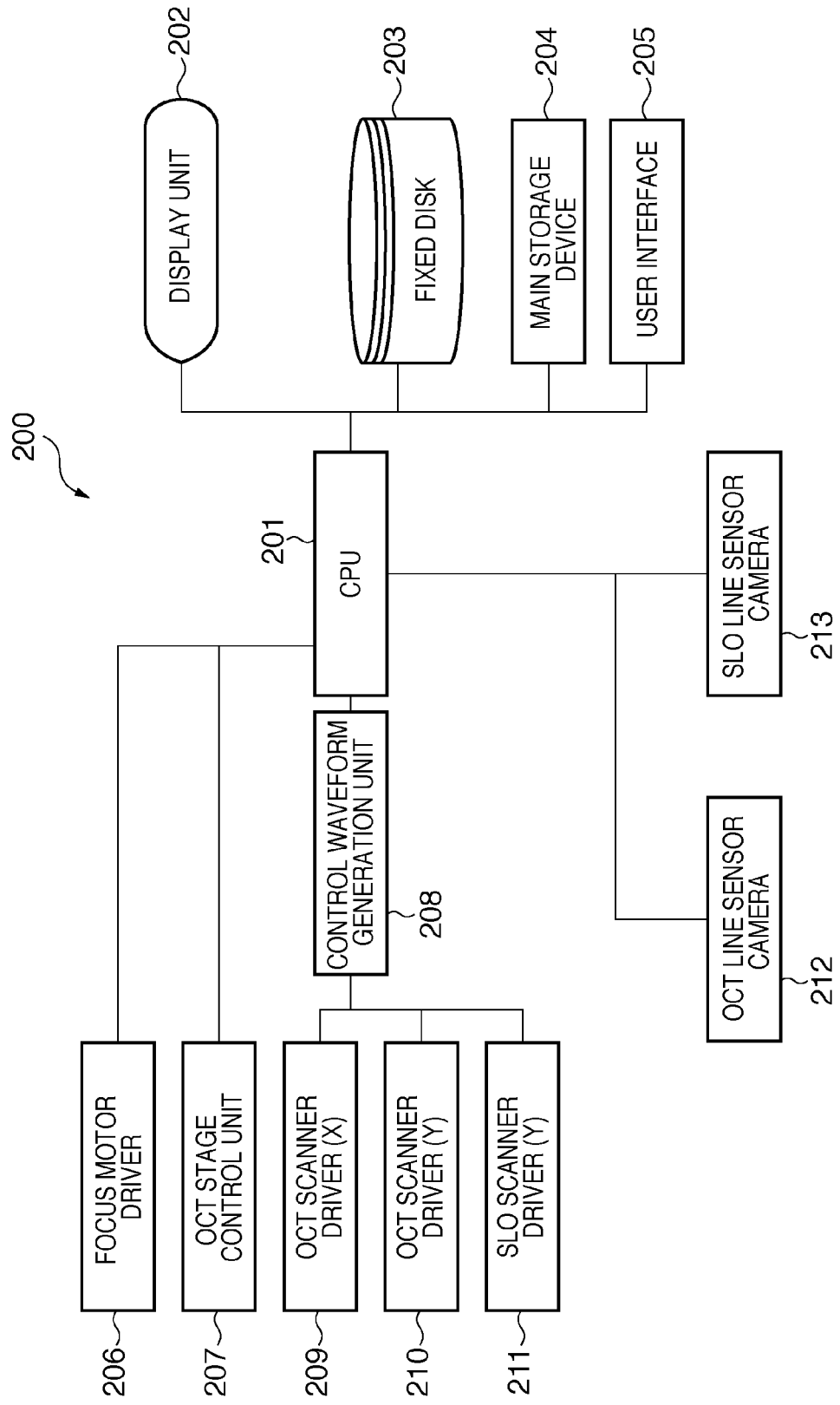
FIG. 2 shows a block diagram of a control unit of the optical coherence tomography in the first embodiment.

The structure of control unit 200 of the optical coherence tomography in the first embodiment is described referring to FIG. 2. FIG. 2 shows a block diagram of the control unit 200 of the optical coherence tomography in this embodiment.

A central processing unit (hereafter CPU 201) is connected to a display unit 202, a fixed disk 203 as an auxiliary storage device, a main storage device 204 (e.g. RAM), a user interface unit 205, a focus motor driver 206 and an OCT stage control unit 207. Further, the CPU 201 is connected to a control waveform generation unit 208 generating a scanning waveform and controls an OCT scanner driver (X) 209, an OCT scanner driver (Y) 210 and an SLO scanner driver 211 via the control waveform generation unit 208. The OCT scanner driver (X) 209, OCT scanner driver (Y) 210 and SLO scanner driver (Y) 211 respectively generate scan-signals to drive the OCT scanner (X) 104, OCT scanner (Y) 107 and SLO scanner (Y) 120. In addition, the CPU 201 is connected to an OCT line sensor camera 212 as the line sensor 114 of the OCT imaging unit and connected to an SLO line sensor camera 213 as the line sensor 131 of the SLO imaging unit.

Figure 3:
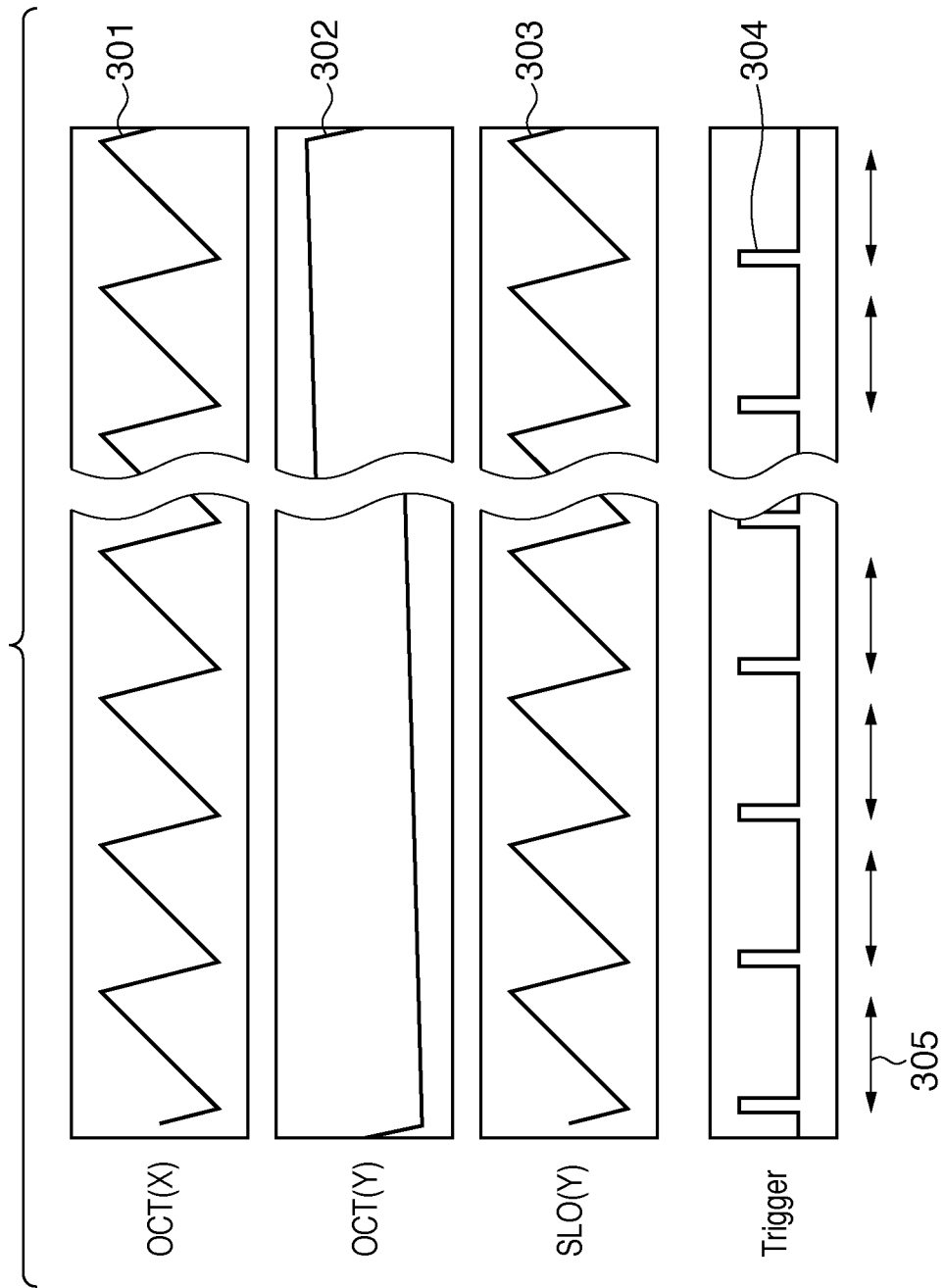
FIG. 3 shows a scan-signal wave of a scanner of the optical coherence tomography in the first embodiment.

Next, a scan-signal waveform is explained referring to FIG. 3, which is supplied to each scanner driver so that the control unit 200 controls each scanner. An OCT (X) scan-signal 301 has a triangle waveform to control the OCT scanner (X) 104 as shown in the figure. An OCT (Y) scan-signal 302 to control the OCT scanner (Y) 107 is a signal to sequentially shift the scanning position of the OCT (X) every period of the OCT (X) scan-signal 301. Although this signal has a slope within the scan coverage in Y-direction, it is not limited to this signal, and for example, a step signal may be utilized, which changes every triangle waveform of the OCT (X) scan-signal 301. The three-dimensional OCT imaging is performed using the scan of the OCT beam by the OCT scanner (X) 104 and OCT scanner (Y) 107. Based on these scan signals, the imaging position of the two-dimensional tomographic image along the first direction (X-direction) obtained by scanning the light (OCT beam) from the low coherent light source 115 in the first direction is repeatedly shifted to the second direction (Y-direction) which is different from the first direction. In this way, a first acquisition process to acquire multiple two-dimensional tomographic images (B-scan images) is performed in order to form a three-dimensional tomographic image. In this embodiment, the three-dimensional tomographic image with high accuracy is obtained by correcting the position of the tomographic image acquired as described above based on the variation of the eyeball detected from the SLO image which is acquired in sync with imaging the tomographic image (described in detail later).

In addition, a step driving with certain constant amplitude is applied to the scanning amount of the OCT scanner (Y) 107 in order to acquire the three-dimensional data in this embodiment. However, the same body part may be repeatedly imaged by setting the scan amount of the OCT scanner (Y) 107, that is, the OCT scanner (Y) scan-signal 302 to zero. In this case, multiple B-scan images corresponding to the same position can be acquired. The purpose for this zero setting is to acquire a B-scan image in high quality by averaging multiple B-scan images obtained by repeatedly imaging the same body part. In this case, the B-scan image in higher quality can be acquired when the B-scan images are excluded from averaging images if the movement of the eyeball obtained from the SLO image is larger than a certain threshold value.

The SLO (Y) scan-signal 303 to control the SLO scanner (Y) 120 has the same scan waveform as the OCT (X) scan-signal 301. That is, the SLO scanner (Y) 120 makes one scan while the OCT scanner (X) 104 makes one scan to acquire one B-scan image, and then the optical system is controlled so that one SLO image is acquired. The B-scan scanning time and SLO scanning time are the same although each scan axis of the B-scan and the SLO scan is different. A synchronized signal for the line sensors 114 (212) and 131 (213) of acquiring these images is a trigger signal 304. At the rising edge of the trigger signal 304, both the line sensor 114 for OCT and the line sensor 131 for SLO start acquiring the data. In this way, the SLO imaging unit, the second acquisition unit acquires a two-dimensional fundus image in sync with imaging a tomographic image by the OCT imaging unit so that one two-dimensional fundus image (an example of cross-over images) is acquired every time one tomographic image is acquired by the OCT imaging unit as the first acquisition unit.

A read-out frequency required for each line sensor is adjusted based on the relation to the resolution, number of pixels or scan rate respectively required for the OCT images and SLO images. The eye to be examined is brought into focus or the display position of the fundus tomographic image is adjusted when the actual image is acquired. In this case, the CPU 201 adjusts the focus using the focus motor driver 206. The focus is then adjusted by moving the eyepiece optical system. For the focus adjustment, an examiner (operator) operates the user interface 205 by verifying the contrast of the SLO image displayed on the display unit 202. That is, the focus is manually adjusted. Further, as for the adjustment of display position of tomographic images, the examiner operates the light path length variable stage 118 using the OCT stage control unit (Z) 207 by verifying the image on the display unit 202 as shown in FIG. 2. These operating instructions are entered from the user interface unit 205. After completing these adjustments, the imaging instruction is entered from the user interface 205 in FIG. 2.

When the imaging instruction is entered by the examiner, a control waveform generation unit 208 in FIG. 2 generates and forms three-dimensional scan waveforms as shown in FIG. 3. Further, multiple B-scan images (tomographic image in X-direction) to form the three-dimensional image and the SLO images (two-dimensional fundus images) corresponding to each B-scan images are acquired and stored. At the rising edge of the trigger signal 304 in FIG. 3, the tomographic images are acquired from the OCT line sensor camera 212 and the two-dimensional fundus images are acquired from the SLO line sensor camera 213, and then the tomographic images and the two-dimensional fundus images are stored. The number "305" in FIG. 3 indicates an image storing period for the tomographic images and two-dimensional fundus images and the image data are stored during the periods indicated with arrows. When the data are stored, the CPU 201 stores the image data acquired by the OCT line sensor camera 212 and the SLO line sensor camera 213 in the fixed disk 203. In this manner, a tomographic image (B-scan image) and the corresponding two-dimensional fundus image (SLO image), which is acquired in sync with the tomographic image, are stored in the fixed disk 203 in pairs. With that, the image acquisition ends.

(Process for Image Correction)

Figure 4:
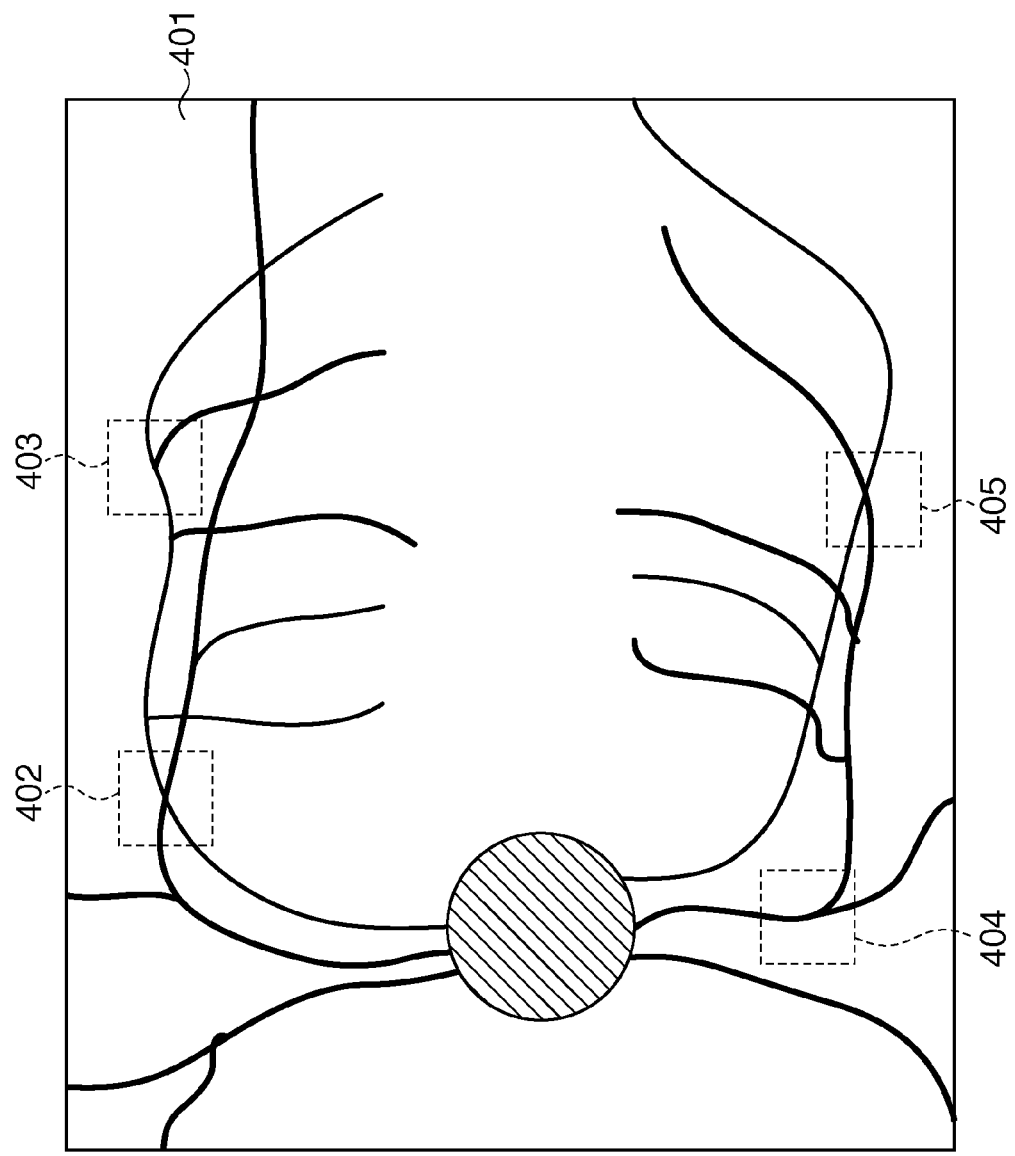
FIG. 4 shows exemplary concept for image correction in the first embodiment.

Next, the process of correcting acquired images is described below referring to FIGS. 4 and 5. FIG. 4 is a figure of explaining image correction in this embodiment. An SLO image 401 is a two-dimensional image of the fundus (two-dimensional fundus image) captured by the SLO imaging unit. Feature points 402 to 405 are extracted from the SLO image 401 in order to measure the movement of the eyeball. These feature points are utilized for the image correction. For example, if a blood vessel cross-over section and a blood vessel bifurcation section are used as feature points, a region including these sections should be extracted. In this embodiment, four feature points are established so that each quadrant referring to the center of the SLO image has one feature point. A standard SLO image is defined as the SLO image from which feature points are extracted. The standard SLO image may be a pre-acquired SLO image, or may be selected from SLO images corresponding to B-scan images for configuring a three-dimensional tomographic image (for example, a top SLO image is selected). Although four feature points are used in this example, it is not limited to four points, and any points more than two that are not on the same line, can be used as feature points.

Figure 5:
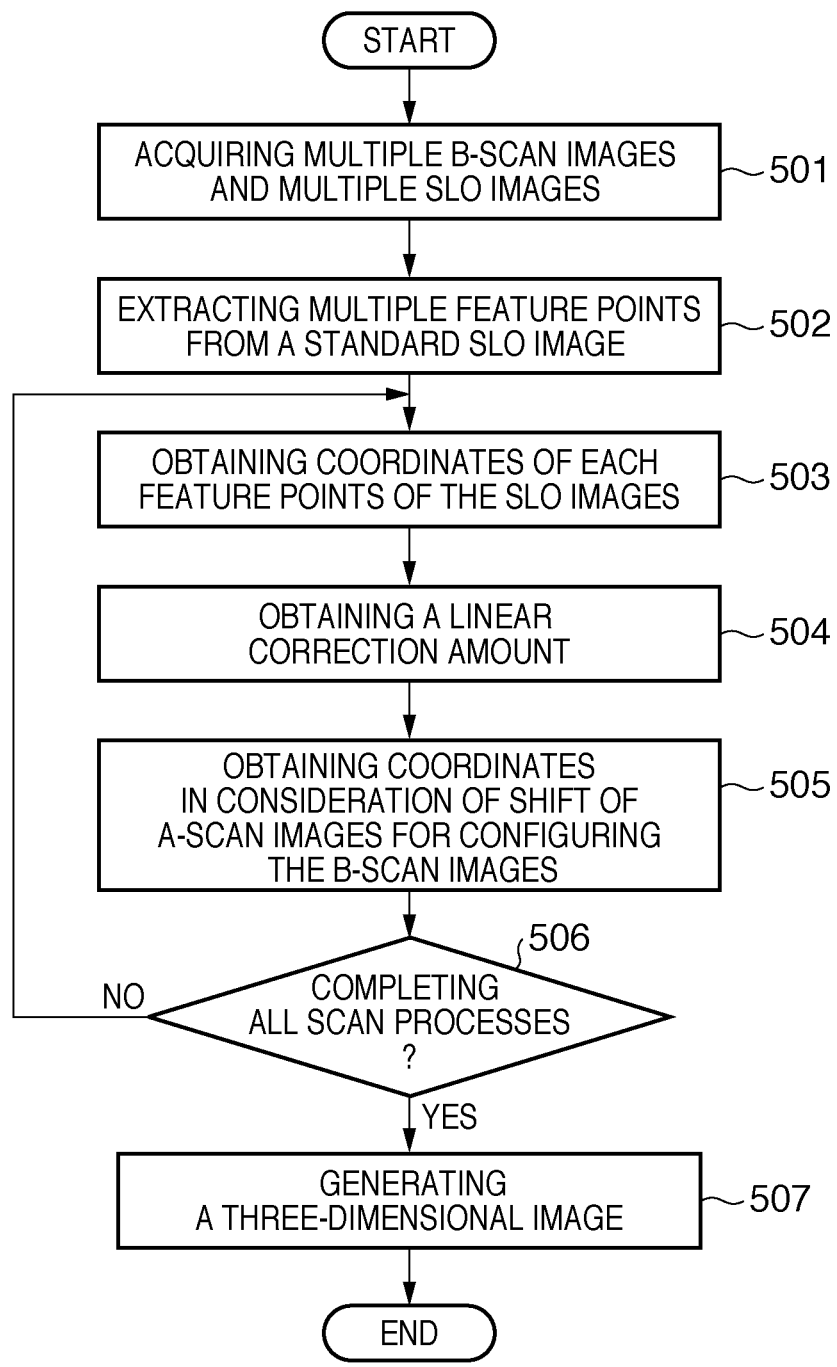
FIG. 5 shows a flowchart indicating the process of correction in the first embodiment.

FIG. 5 shows the flowchart indicating image correction in this embodiment. Further, each step of the following processes is implemented by CPU 201.

At step 501, based on the imaging operations as described above, the CPU 201 stores multiple B-scan images used to form a three-dimensional tomographic image and multiple two-dimensional fundus images corresponding to the B-scan images. At step 502, the CPU 201 extracts multiple feature points corresponding to the feature points 402 to 405 in FIG. 4 from the standard SLO image and memorizes the feature point-coordinate on the standard SLO image. More specifically, the CPU 201 memorizes a standard position which is coordinates of the feature point (XiRef, YiRef), (where i is the number of feature point) and a shape of the feature point.

At step 503, the CPU 201 obtains the positions of all feature points (Xi, Yi) in the SLO image acquired in sync with the B-scan image. For example, a well-known pattern matching process using the above shape of feature point can be applied to detect the positions of feature points. At step 504, the CPU 201 detects the variance of the position of the extracted feature point and obtains a correction amount for one B-scan image based on the detected variation. More specifically, for example, the CPU 201 obtains a mapping coordinate based on each displacement of the feature points using Equation (1) and calculates a linear correction amount so that the difference between the mapping coordinate and the acquired image coordinate of the feature points is minimized. The linear correction amount is obtained by the least –square method using each of the magnification (Magnification), the rotation amount (θ) and the parallel shift amount (ShiftX, ShiftY) defined in the following linear mapping equation (the linear correction amount which makes Equation (2) minimum is obtained):

Equation (1)

$$\begin{pmatrix} MapXi \\ MapYi \end{pmatrix} = \text{Magnification} \begin{pmatrix} \cos\theta & -\sin\theta \\ \sin\theta & \cos\theta \end{pmatrix} \begin{pmatrix} XiRef \\ YiRef \end{pmatrix} + \begin{pmatrix} ShiftX \\ ShiftY \end{pmatrix} \quad (1)$$

Equation (2)

$$\sum_{i=1}^{n} ((MapXi - Xi)^2 + (MapYi - Yi)^2) \quad (2)$$

(where n is the number of feature points.)

That is, the CPU 201 obtains the correction amount which can represent the shift amounts of n feature points with minimum errors. At step 505, the CPU 201 obtains the acquired position of the B-scan image in consideration of shift using the obtained linear correction amount (Equation (3)).

Equation (3)

$$\begin{pmatrix} CorrectX \\ CorrectY \end{pmatrix} = \text{Magnification} \begin{pmatrix} \cos\theta & -\sin\theta \\ \sin\theta & \cos\theta \end{pmatrix} \begin{pmatrix} X \\ Y \end{pmatrix} + \begin{pmatrix} ShiftX \\ ShiftY \end{pmatrix} \quad (3)$$

Let the position of A-scan images for configuring B-scan images be (X, Y) when there is no movement of the eyeball, and then the position of the acquired B-scan image in consideration of the correction amount can be obtained by Equation (3). Where, the positions of all A-scan images for generating a B-scan image are obtained by applying the calculated correction amount for the corresponding two-dimensional fundus image. At step 506, the CPU 201 determines whether or not all the B-scan images are processed, and if there is an unprocessed B-scan image, control returns to step 503 and a process for the next B-scan image starts. After the above steps are repeatedly performed for all B-scan images, the B-scan images for configuring a three-dimensional tomographic image can be corrected and placed at the position based on the eyeball position when the B-scan image was acquired. If the process of all B-scan images is complete, at step 507, the three-dimensional tomographic image for observation is generated by using the corrected B-scan images. Thus, the three-dimensional tomographic image is generated after the relative position between multiple B-scan images are adjusted based on the acquired two-dimensional fundus images in synchronization by acquiring each of the corresponding B-scan images for configuring the three-dimensional tomographic image. By virtue of this arrangement, the three-dimensional shift can be corrected with high accuracy.

Although all B-scan images are assumed to be acceptable in the embodiment as described above, it may be determined that a B-scan is not used for the correction if the correction amounts (Magnification, θ, ShiftX, ShiftY) of the B-scan image exceeds certain threshold values. For example, it is considered that there must be a large movement of the eyeball if the correction amount exceeds the certain threshold value. In addition, whether the correction amounts exceeds the certain threshold values is determined based on the variation from the standard image, and may also be determined based on the difference between a B-scan image and the previous B-scan image (the image acquired immediately before the B-scan image or the image acquired before certain numbers of scans). By adding this process, it is possible to appropriately delete the data even if there has been a large movement of the eyeball such as a micro-saccade in one B-scan image. Further, it may be determined by referring to the variation value instead of the correction amount whether or not the B-scan image is utilized.

Further, although the correction amount is determined by acquiring one two-dimensional fundus image corresponding to one B-scan image, it may be determined by acquiring one two-dimensional fundus image corresponding to more than one B-scan image. That is, n B-scan images may be corrected based on the correction amounts obtained by acquiring one two-dimensional fundus image corresponding to the n B-scan images. At this time, various methods are considered to determine the correction amount to apply the n B-scan images. For example, the common correction amount may be applied to all the n B-scan images, where the common correction amount is calculated by using the above method based on the two-dimensional fundus images that are acquired by the SLO imaging unit in sync with any one of the n B-scan images. For example, a top image of the n B-scan images may be selected as the any one of the n B-scan images. Moreover, by setting a period of acquiring the n B-scan images to be equal to one scan period of the SLO beam, one two-dimensional fundus image can be obtained for n B-scan images, and the correction amount may be obtained based on the one two-dimensional fundus image after acquiring the two-dimensional fundus image corresponding to the n B-scan images.

Second Embodiment

Next, an optical coherence tomography in a second embodiment is described below.

(Optical Structure of OCT Imaging Unit)

Figure 6:
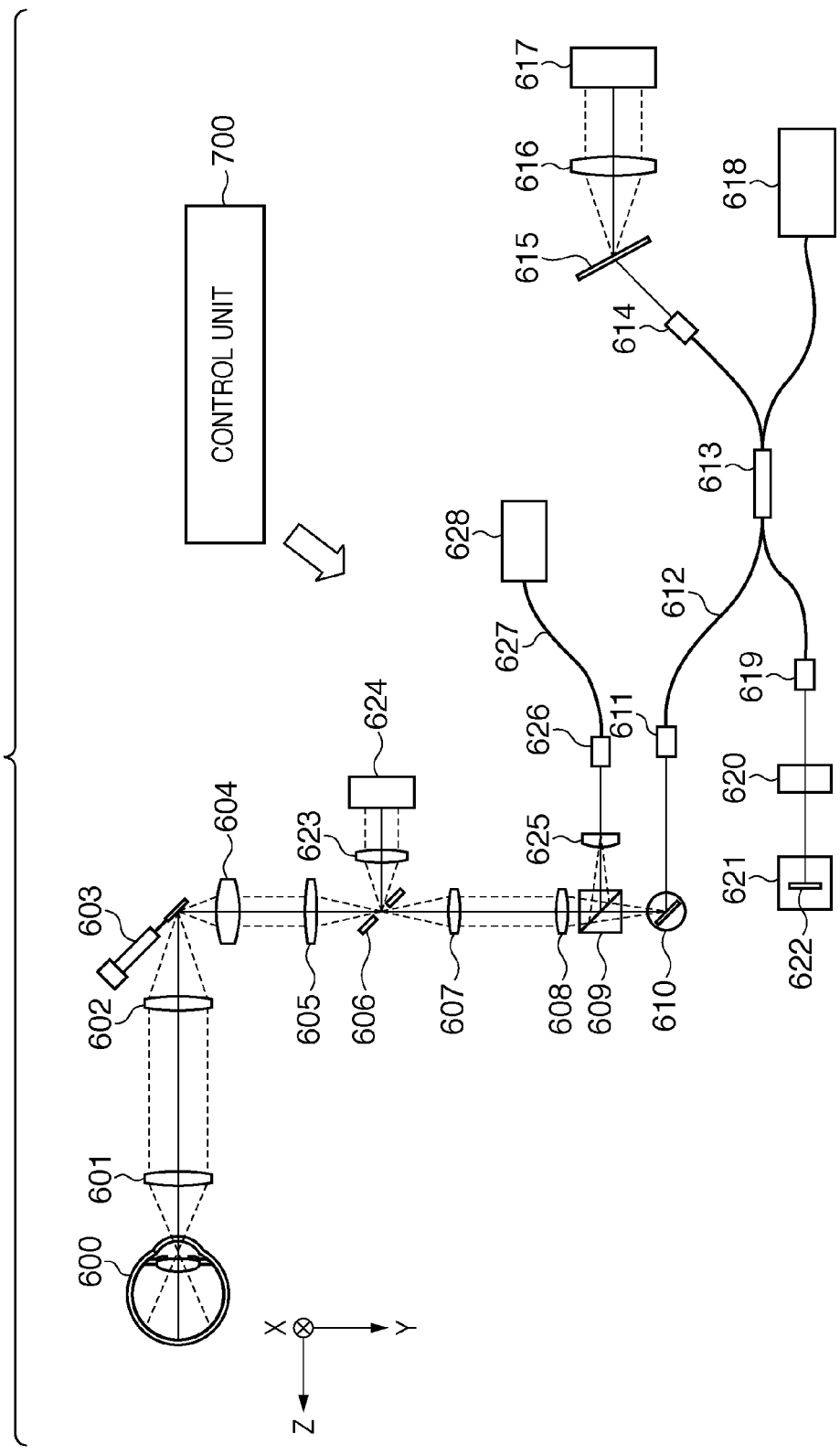
FIG. 6 shows an exemplary configuration for an optical system of optical coherence tomography in the second embodiment.

An OCT imaging unit in the second embodiment is described referring to FIG. 6. For example, a super luminescent diode with a central wavelength of 840 nm and a wavelength half-width of 45 nm is used as a low coherent light source 618. Low coherent light emitted from the low coherent light source 618 enters a fiber coupler 613 via an optical fiber and is separated into measurement light and reference light. The measurement light in a form of parallel light beam is emitted from a fiber collimator 611 through an optical fiber 612, and passes through a scanner (Y) 610 (an example of a second scan unit), a dichroic beam splitter 609, relay lenses 608, 607, a ring mirror 606 and relay lenses 605, 604. Further, the measurement light passes through a scanner (X) 603 (an example of first scan unit) and is incident on an examined eye 600 after passing through a scan lens 602 and an eyepiece lens 601. The light incident on the examined eye 600 reflects on the retina and returns back to the fiber coupler 613 after passing through the same light path. By operating the scanner (Y) 610, the measurement light is scanned toward the vertical direction (Y-direction) when the subject being examined is upright. By operating the scanner (X) 603, the measurement light is scanned toward the horizontal direction (X-direction) when the subject being examined is upright.

The reference light is guided from a fiber coupler 613 to a fiber collimator 619, and it is emitted after becoming a parallel light. The emitted reference light reflects on a reference mirror 622 that is arranged in a light path-length variable stage 621 after passing through a dispersion correction glass 620. The reference light reflected from the reference mirror 622 returns to the fiber coupler 613 after passing through the same light path.

The measurement light and reference light returned to the fiber coupler 613 are guided to the fiber collimator 614 after they are combined by the fiber coupler 613. Here, the combined light is defined as interference light. A spectrometer comprises the fiber collimator 614, a transmission grating 615, a lens 616 and a line sensor 617. The spectrometer measures the interference light as intensity information corresponding to every wavelength.

(Optical Structure of SLO Imaging Unit)

The optical structure of SLO imaging unit is described with referring to FIG. 6. A semiconductor laser with a wavelength of 760 nm is used as the laser light source 628. Laser light emitted from the laser light source 628 becomes a parallel light after passing through a fiber collimator 626 via an optical fiber 627 and it is incident upon a cylinder lens 625. The laser light is linearly spread out toward Y-direction by the cylinder lens 625 and reflected on the dichroic beam splitter 609 (an example of the light path split unit). The dichroic beam splitter 609 has a film which transmits light with wavelengths equal to or greater than 800 nm and reflects light with wavelengths below 770 nm. A beam reflected on the dichroic beam splitter 609 passes through relay lenses 607, 608, the center of a ring mirror 606, relay lenses 605, 604 and the scanner (X) 603 (one example of the first scan unit) that is shared with the OCT imaging unit. Further, this beam is incident upon the examined eye 600 after passing through a scan lens 602 and an eyepiece lens 601. In this manner, the OCT imaging unit and the SLO imaging unit use the scanner (X) 603 as a common scan mechanism and perform the scan toward the X-direction.

A line beam extending toward a vertical direction (Y) is projected on the fundus of the examined eye 600. The line beam reflected or scattered on the fundus of the examined eye 600 returns back to the ring mirror 606 after passing through the same light path. Because the position of the ring mirror 606 is conjugate with the pupil position of the examined eye, light passing through the peripheral part of the pupil among the back scattering light of the line beam irradiated on the fundus is reflected on the ring mirror 606 and it forms an image on the line sensor 624 after passing through a lens 623. As described above, the SLO imaging unit in this embodiment is configured with the line-scan SLO using line beams. In this case, the scanner (X) 603 is shared with the SLO imaging unit and the OCT imaging unit in this embodiment. By virtue of this arrangement, the line beam of the SLO imaging unit spread out toward the vertical direction (Y-direction) when the subject is upright and the beam of the measurement light are steadily and synchronously scanned toward the X-direction. In addition, the line beam of the SLO imaging unit and the line beam of measurement light of the OCT imaging unit may not need to be placed at the same X coordinate. That is, they may be shifted in the X-direction. In other words, the scan period of the line beams of the SLO imaging unit and OCT imaging unit only needs to be synchronized. Imaging operations using the optical system of OCT imaging unit and the optical system of SLO imaging unit are controlled by the control unit 700.

(Structure of Control Unit)

Figure 7:
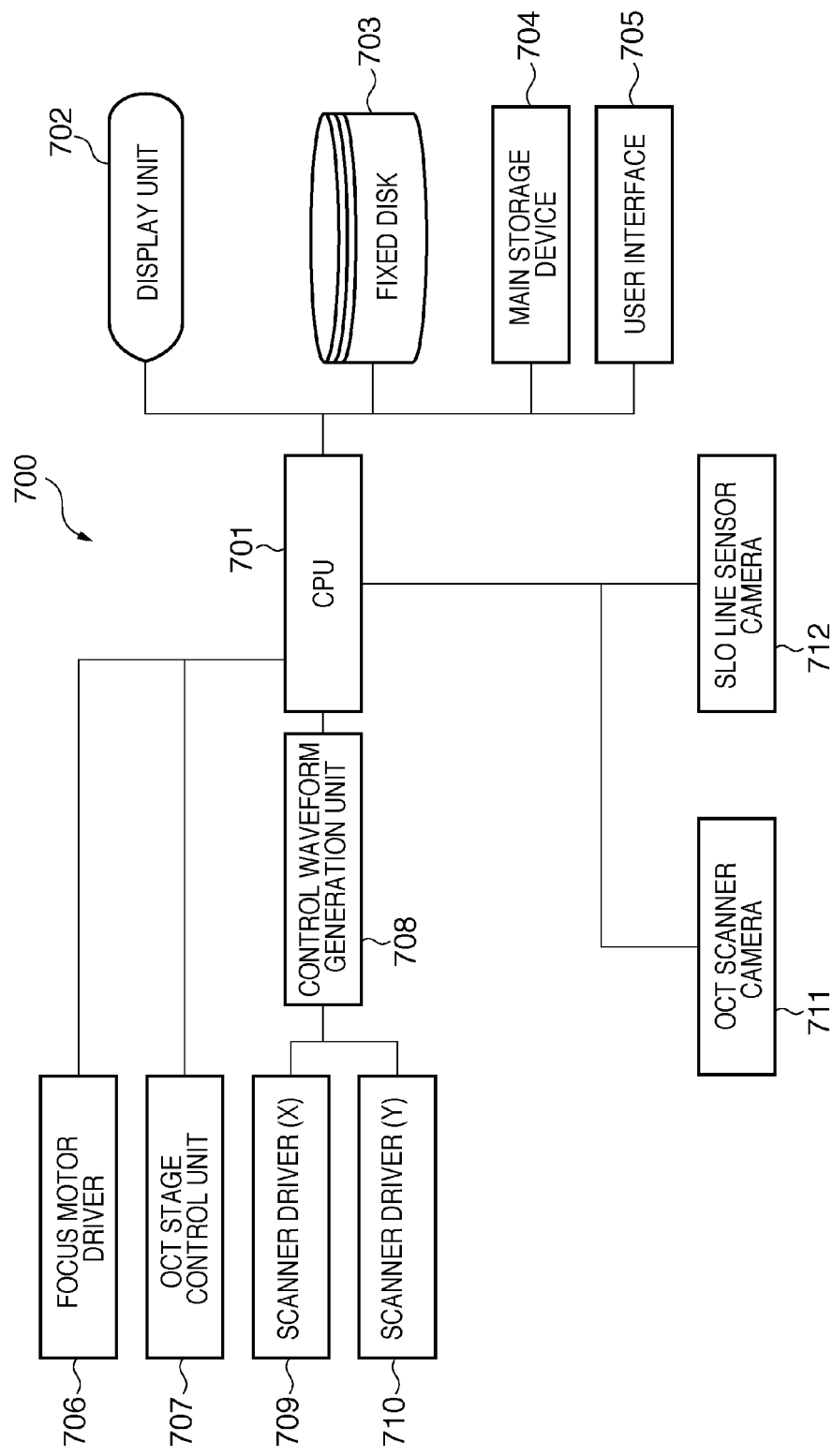
FIG. 7 shows a block diagram of a control unit of the optical coherence tomography in the second embodiment.

Next, the structure of control unit 700 is described referring to FIG. 7. FIG. 7 shows a block diagram of the control unit of the optical coherence tomography in this embodiment.

A central processing unit (hereafter CPU 701) is connected to a display unit 702, a fixed disk 703 as an auxiliary storage device, a main storage device 704 (e.g. RAM) and a user interface unit 705. Further, the CPU 701 is connected to a focus motor driver 706 and an OCT stage control unit 707. Moreover, the CPU 701 is connected to a control waveform generation unit 708 generating a scanning waveform and controls a scanner driver (X) 709, a scanner driver (Y) 710 via the control waveform generation unit 708. In addition, the CPU 701 is connected to an OCT line sensor camera 711 as the line sensor 617 of the OCT imaging unit and connected to an SLO line sensor camera 712 as the line sensor 624 of the SLO imaging unit.

Next, the method of controlling image capturing in the second embodiment is described using FIGS. 7 and 8. At the time of capturing the three-dimensional image, each scanner is controlled by using the control waveforms indicated in FIG. 8.

An OCT (X) scan signal 801 has a triangle waveform shown in FIG. 8 which controls the scanner (X) 603 to scan the measurement beam of the OCT imaging unit and the beam of the SLO imaging unit in X-direction. A scanner (Y) scan signal 802 is a signal to shift the scan position every period of the scanner (X) scan signal 801, where the scanner (Y) scan signal 802 controls the scanner (Y) 610 to shift the measurement beam of the OCT imaging unit in Y-direction. Although this signal has a slope within the scan region in Y-direction, it is not limited to this signal, and for example, a step signal, which changes every triangle waveform of the OCT (X) scan-signal 801, may be utilized. The three-dimensional OCT image capturing can be performed using the scan of the OCT beam by the OCT scanner (X) 603 and OCT scanner (Y) 610. Further, by scanning of the scanner (X) 603, an SLO image is acquired in sync with a B-scan image. A trigger signal 803 is a signal to synchronize each line sensor for acquiring these images, and at the rising edge of the trigger signal 803, both the line sensor 617 for OCT and line sensor 624 for SLO start acquiring the data. In this way, the SLO imaging unit, the second acquisition unit acquires a two-dimensional fundus image in sync with imaging a tomographic image by the OCT imaging unit so that one two-dimensional fundus image (an example of cross-over images) is acquired every time one tomographic image is acquired by the OCT imaging unit, the first acquisition unit.

A read-out frequency required for the OCT line sensor 617 and SLO line sensor 624 is adjusted based on the relation with resolution, number of pixels or scan rate respectively required for the OCT images and SLO images. The examined eye 600 is brought into focus or the display position of the fundus tomographic image is adjusted when actual image is captured. In this case, the focus motor driver 706 adjusts the focus by moving the eyepiece optical system. For the focus adjustment, the examiner operates the user interface 705 by verifying the contrast of the SLO image displayed on the display unit 702. Further, as for the adjustment of display position of tomographic images, the examiner operates the light path length variable stage 621 in FIG. 6 using the OCT stage control unit (Z) 707 in FIG. 7 by verifying the image on the display unit 702 as shown in FIG. 7. These operating instructions are entered from the user interface unit 705. After completing these adjustments, the examiner enters the imaging instruction using the user interface 705.

When the imaging instruction is entered, the CPU 701 controls a control waveform generation unit 708 in FIG. 7 to generate three-dimensional scan waveforms in FIG. 8, and acquires and stores multiple B-scan images to generate the three-dimensional image and the SLO images corresponding to each B-scan images. At the rising edge of the trigger signal 803, the data are acquired and stored after the OCT line sensor camera 711 (617) and the SLO line sensor camera 712 (624) respectively capture the images. The reference numeral "804" in FIG. 8 indicates an image storing period for the B-scan images of the OCT imaging unit and SLO images of the SLO imaging unit, and the data are stored during these periods indicated by arrows. When the data is stored, the CPU 701 stores the image data acquired by the OCT line sensor camera 711 and the SLO line sensor camera 712 in the fixed disk 703. With that, we come to the end of the image acquisition. In addition, a tomographic image (B-scan image) and the corresponding two-dimensional fundus image (SLO image) which is acquired in sync with the tomographic image are stored in the fixed disk 703 in pairs.

(Process for Image Correction)

Next, the image correction in the second embodiment is explained. The process of correcting acquired images in the second embodiment is described referring to FIGS. 4 and 5 of the first embodiment. In the second embodiment, the components of the rotation amount and the magnification are separated into two axes comprising the first direction (X-direction) and the second direction (Y-direction), and they are calculated by using a linear mapping equation. Further, each step of the following processes is implemented by CPU 701.

At step 501, based on the operations as described in FIGS. 6, 7 and 8, multiple B-scan images and multiple two-dimensional fundus images (SLO images) are stored in the fixed disk 703. At step 502, the CPU 701 extracts multiple feature points corresponding to the feature points 402 to 405 in FIG. 4 from the standard SLO image and stores the feature point-coordinate on the standard SLO image. More specifically, the CPU 701 memorizes a standard position which is a coordinates of the feature point (XiRef, YiRef), (where i is the number of feature point) and a shape (pattern) of the feature point.

At step 503, the CPU 701 obtains the positions of all feature points (Xi, Yi) in the SLO image acquired in sync with the B-scan image. At step 504, the CPU 701 detects the variance of the position of the extracted feature point and obtains a correction amount for one B-scan image based on the detected variation. More specifically, for example, the CPU 701 obtains a mapping coordinate based on each displacement of the feature points using Equation (4) and calculates a linear correction amount so that the difference between the mapping coordinate and the acquired image coordinate of the feature points is minimized. The CPU 701 obtains the linear correction amount by a least –square method using each of the rotation amount ($\theta x$, $\theta y$), the magnification (MagnificationX, MagnificationY), and the parallel shift amount (ShiftX, ShiftY) defined in the following linear mapping equation (the linear correction amount which makes Equation (5) minimum is obtained):

Equation (4)

$$\begin{pmatrix} MapXi \\ MapYi \end{pmatrix} = \begin{pmatrix} MagnificationX & 0 \\ 0 & MagnificationY \end{pmatrix} \begin{pmatrix} \cos\theta x & -\sin\theta x \\ \sin\theta y & \cos\theta y \end{pmatrix} \begin{pmatrix} XiRef \\ YiRef \end{pmatrix} + \begin{pmatrix} ShiftX \\ ShiftY \end{pmatrix}$$

Equation (5)

$$\sum_{i=1}^{n} ((MapXi - Xi)^2 + (MapYi - Yi)^2)$$

(where n is the number of feature points.)

That is, the CPU 701 obtains the correction amount which can represent the shift amounts of n feature points with minimum errors. The difference of the correction process from the first embodiment is that the correction amount is calculated after the components of the rotation amount and magnification are separated into the first direction (X) and the second direction (Y). In addition, the calculation method of correction amount in the first embodiment may be applied to the second embodiment, and adversely, the calculation method of correction amount in the second embodiment may be applied to the first embodiment.

At step 505, the CPU 701 obtains the acquired position of the B-scan image in consideration of the shift using the obtained linear correction amount (Equation (6)).

Equation (6)

$$\begin{pmatrix} CorrectX \\ CorrectY \end{pmatrix} = \begin{pmatrix} MagnificationX & 0 \\ 0 & MagnificationY \end{pmatrix} \begin{pmatrix} \cos\theta x & -\sin\theta x \\ \sin\theta y & \cos\theta y \end{pmatrix} \begin{pmatrix} X \\ Y \end{pmatrix} + \begin{pmatrix} ShiftX \\ ShiftY \end{pmatrix}$$

Let the position of A-scan images for configuring B-scan images be (X, Y) when there is no movement of the eyeball, and then the position of the acquired B-scan image in consideration of the correction amount can be obtained by Equation (6). In this embodiment, the positions of all A-scan images for configuring B-scan images are obtained by applying the calculated correction amount. At step 506, the CPU 701 determines whether or not all the B-scan images are processed, and if there is an unprocessed B-scan image, the control returns to step 503 and the process for the next B-scan image starts.

After the process of all the B-scan images is complete, at step 507, the CPU 701 generates a three-dimensional tomographic image by using the corrected B-scan images. After this step, the process ends. After the above steps are repeatedly performed for all B-scan images, the B-scan images for configuring a three-dimensional tomographic image can be corrected and be placed at the position based on the eyeball position when the B-scan image was acquired. Therefore, at step 507, the three-dimensional tomographic image is generated by multiple B-scan images (tomographic image) whose relative positions are adjusted Although all B-scan images are assumed acceptable in this embodiment as described above, it may be determined that a B-scan should be deleted as invalid data if the difference between θx and θy or MagnificationX and MagnificationY in each correction amount of the B-scan images exceeds a certain threshold value because there is large movement of the eyeball. By adding this process, it is possible to appropriately exclude unwanted data even if there is a large movement of the eyeball such as a micro-saccade in one B-scan image.

As mentioned in the first embodiment, the n tomographic images (B-scan images) may be acquired corresponding to one two-dimensional fundus image (SLO image).

In addition, the process of steps 503 to 507 in the above embodiments may be performed by a information processing device such as a personal computer. In that case, the tomographic images and two-dimensional fundus images stored in the fixed disk 203, 703 are provided to the information processing device, and the information processing device generates the three-dimensional tomographic image using these images.

As mentioned above, according to the above embodiments, the optical coherence tomography enables to correct the variation of tomographic images with higher accuracy generated by the movement of the examined eye during shooting where multiple tomographic images are acquired by the optical coherence tomography using light interference. Specifically, the optical coherence tomography can correct the variation of the tomographic image with higher accuracy caused by the movement of examined eye during shooting when the three-dimensional image is generated by using tomographic images acquired by the optical coherence tomography using light interference.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer, for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-150261, filed Jun. 30, 2010, which is hereby incorporated by reference herein in its entirety.

The invention claimed is:

1. An image sensing apparatus comprising:
   a first scan unit configured to scan light from an OCT light source and a line beam from an SLO light source in a first direction of an eye, wherein the first direction corresponds to a main scanning direction of the light from the OCT light source and a direction that intersects a line direction of the line beam from the SLO light source;
   a second scan unit configured to scan the light from the OCT light source in a second direction different from the first direction of the eye, wherein the second direction corresponds to a sub scanning direction of the light from the OCT light source;
   a first acquisition unit configured to acquire tomographic images of the eye along the first direction when the first scan unit scans the light from the OCT light source; and
   a second acquisition unit configured to acquire fundus images of the eye corresponding to the tomographic images when the first scan unit scans the line beam from the SLO light source,
   wherein the first scan unit includes a common scan mechanism for the line beam from the SLO light source and the light from the OCT light source.

2. The apparatus according to claim 1, further comprising:
   a light path split unit, which is arranged on a light path guiding the light from the second scan unit to the first scan unit; and
   an optical element which forms the line beam from light from the SLO light source,
   wherein the light path split unit guides the line beam to the first scan unit.

3. The apparatus according to claim 1, further comprising:
   a detection unit configured to extract feature points from each of the fundus images acquired by the second acquisition unit and to detect variation of the feature points in the fundus images; and
   a generation unit configured to generate an image for observation using the tomographic images and the variation of the feature points detected by the detection unit.

4. The apparatus according to claim 3, wherein the first acquisition unit acquires multiple tomographic images usable for generating a three-dimensional tomographic image by scanning the light from the OCT light source in the first direction by the first scan unit and repeating the scan while shifting scan position to the second direction by the second scan unit, and
   wherein the generation unit comprises a unit configured to generate a three-dimensional tomographic image as the image for observation by correcting the position of the tomographic images in the three-dimensional tomographic image based on the variation.

5. The apparatus according to claim 4, wherein the line beam from the SLO is extended to the second direction, and the fundus image is acquired by scanning the line beam to the first direction, and
   wherein the scan of the light from the OCT light source in the first acquisition unit to the first direction and the scan of the line beam to the first direction are simultaneously performed.

6. The apparatus according to claim 4, wherein the generation unit:
   calculates correction amount to correct variation of the position of feature points for each fundus image acquired by the second acquisition unit; and generates the three-dimensional tomographic image by correcting the tomographic images acquired during the period corresponding to each fundus image using the calculated correction amount for each fundus image.

7. The apparatus according to claim 6, wherein the generation unit calculates the correction amount for magnification, rotation, and translation using a linear mapping equation.

8. The apparatus according to claim 7, wherein the linear mapping equation is configured to calculate the correction amount for the rotation and magnification using their components separated into the first direction and the second direction.

9. The apparatus according to claim 6, wherein the generation unit does not use the tomographic image for the three-dimensional tomographic image, which has been acquired during the period corresponding to the fundus image and has the variation amount or the correction amount exceeding a certain threshold value.

10. The apparatus according to claim 1, wherein the second acquisition unit acquires fundus images in sync with the acquisition of tomographic images in the first acquisition unit so as to acquire one fundus image every N tomographic images.

11. The apparatus according to claim 3, wherein the first acquisition unit obtains multiple tomographic images by repeating the scan of the light from the OCT light source to the first direction at the same position, and
wherein the generation unit generates the image for observation by averaging the multiple tomographic images, and excludes the tomographic image from the object of averaging, which has been acquired during the period corresponding to the feature point and has the large variation.

12. A method of controlling an image sensing apparatus, comprising:
a first scanning step of scanning light from an OCT light source and a line beam from an SLO light source in a first direction of an eye using a first scanning unit, wherein the first direction corresponds to a main scanning direction of the light from the OCT light source and a direction that intersects a line direction of the line beam from the SLO light source;
a second scanning step of scanning the light from the OCT light source in a second direction different from the first direction of the eye using a second scanning unit, wherein the second direction corresponds to a sub scanning direction of the light from the OCT light source;
a first acquiring step of acquiring tomographic images of the eye along the first direction when scanning the light from the OCT light source in the first scanning step; and
a second acquiring step of acquiring fundus images of the eye corresponding to the tomographic images when scanning the line beam from the SLO light source in the first scanning step,
wherein, in the first scan step, the line beam from the SLO light source and the light from the OCT light source are scanned using a common scan mechanism.

13. A non-transitory computer readable medium in which a computer program that causes a computer to execute the method according to claim 12 is stored.

14. The apparatus according to claim 2, further comprising a line sensor which detects a light returning from the eye on which the line beam is illuminated.

15. The apparatus according to claim 1, further comprising a unit configured to transmit the light from the OCT light source via the second scan unit and to reflect the line beam from the SLO light source.

16. The apparatus according to claim 1, further comprising a unit configured to reflect the light from the OCT light source via the second scan unit and to transmit the line beam from the SLO light source.

17. An image sensing apparatus comprising:
a first scan unit that includes a common scan mechanism for light from an OCT light source and light from an SLO light source, and is configured to scan light from the OCT light source and light from the SLO light source in a first direction with respect to an eye;
a second scan unit configured to scan light from the OCT light source in a second direction different from the first direction, wherein the second scan unit is arranged in an OCT optical system including the OCT light source and the first scan unit, and arranged outside a common optical path of an SLO optical system including the SLO light source and the first scan unit and the OCT optical system;
a first acquisition unit configured to acquire a tomographic image of the eye along the first direction by scanning light from the OCT light source using the first scan unit; and
a second acquisition unit configured to acquire a fundus image of the eye corresponding to the tomographic image by scanning light from the SLO light source using the first scan unit.

18. A method of controlling an image sensing apparatus comprising a first scan unit that includes a common scan mechanism for light from an OCT light source and light from an SLO light source, and is configured to scan light from the OCT light source and light from the SLO light source in a first direction with respect to an eye, and a second scan unit configured to scan light from the OCT light source in a second direction different from the first direction, wherein the second scan unit is arranged in an OCT optical system including the OCT light source and the first scan unit, and arranged outside a common optical path of an SLO optical system including the SLO light source and the first scan unit and the OCT optical system, said method comprising:
a first acquisition step of acquiring a tomographic image of the eye along the first direction by scanning light from the OCT light source using the first scan unit; and
a second acquisition step of acquiring a fundus image of the eye corresponding to the tomographic image by scanning light from the SLO light source using the first scan unit.

19. A non-transitory computer readable medium storing a program for causing a computer to execute each step of a method of controlling the image sensing apparatus according to claim 18.

20. The apparatus according to claim 1, wherein the first acquisition unit acquires the tomographic image and the second acquisition unit acquires the fundus image, based on light returned from the eye irradiated with light from the OCT light source via the first scan unit and the second scan unit, irradiated with light from the SLO light source via the first scan unit, and simultaneously irradiated with both light from the OCT light source and light from the SLO light source.

21. The method according to claim 12, wherein the first acquisition step acquires the tomographic image and the second acquisition step acquires the fundus image, based on light returned from the eye irradiated with light from the OCT light source via the first scan unit and the second scan unit, irradiated with light from the SLO light source via the first scan unit, and simultaneously irradiated with both light from the OCT light source and light from the SLO light source.

22. The apparatus according to claim 17, wherein the first acquisition unit acquires the tomographic image and the second acquisition unit acquires the fundus image, based on light returned from the eye irradiated with light from the OCT light source via the first scan unit and the second scan unit, irradiated with light from the SLO light source via the first scan unit, and simultaneously irradiated with both light from the OCT light source and light from the SLO light source.

23. The method according to claim 18, wherein the first acquisition step acquires the tomographic image and the second acquisition step acquires the fundus image, based on light returned from the eye irradiated with light from the OCT light source via the first scan unit and the second scan unit, irradiated with light from the SLO light source via the first scan unit, and simultaneously irradiated with both light from the OCT light source and light from the SLO light source.

* * * * *